(12) United States Patent
Spielberg

(10) Patent No.: US 7,875,072 B2
(45) Date of Patent: Jan. 25, 2011

(54) CELLULAR TRANSPLANT STENT

(76) Inventor: Theodore E. Spielberg, 10 Pinewood Cir., Wellesley, MA (US) 02181

( * ) Notice: Subject to any disclaimer, the term of this patent is extended or adjusted under 35 U.S.C. 154(b) by 681 days.

(21) Appl. No.: 11/691,147

(22) Filed: Mar. 26, 2007

(65) Prior Publication Data

US 2008/0243235 A1 Oct. 2, 2008

(51) Int. Cl.
*A61F 2/06* (2006.01)
(52) U.S. Cl. ...................... 623/1.41; 623/1.42
(58) Field of Classification Search ................ 623/1.15, 623/1.42, 1.41; 424/423; 606/192
See application file for complete search history.

(56) References Cited

U.S. PATENT DOCUMENTS

| 7,037,319 B2 * | 5/2006 | Weber ..................... 606/192 |
| 2002/0007209 A1 * | 1/2002 | Scheerder et al. .......... 623/1.15 |
| 2003/0120339 A1 * | 6/2003 | Banik et al. ................ 623/1.42 |
| 2006/0280768 A1 * | 12/2006 | Hwang et al. ............... 424/423 |

* cited by examiner

*Primary Examiner*—Corrine M McDermott
*Assistant Examiner*—Matthew Schall
(74) *Attorney, Agent, or Firm*—Cesari and McKenna, LLP; Martin J. O'Donnell

(57) ABSTRACT

A cellular stent carries living therapeutic cellular material for implantation into a human or animal body and allows either localized or systemic delivery of the therapeutic products, while promoting engraftment, either on a tissue surface or its interior. The cells are contained within wells in the stent that are enclosed by inner and outer membranes that seal the cellular material within the stent until it is to be released. The outer membrane is preferably in the form of a thin, hard plastic sheet having a plurality of score lines, perforations, or other lines or weakening provided therein. The membrane may be embedded in a softer perimetral mount which retains it in position until the seal is to be broken. Rupture of the outer membrane ensures penetration of the cells into the interior of tissue or an organ in which the stent is implanted.

21 Claims, 1 Drawing Sheet

CELLULAR TRANSPLANT STENT

BACKGROUND OF THE INVENTION

1. Field of the Invention

The invention relates to stents and more particularly comprises a stent which facilitates cellular transplant at the surface or interior of a tissue or organ.

2. Background Information

Stents are commonly used to support bodily structures, such as blood vessels, bile ducts and pancreatic ducts, as well as ureters and bladders. Typically such stents consist of an expansible mesh which is collapsible during insertion, and thereafter expansible (ex. by means of a balloon catheter) to firmly engage the inner wall surface of the structure and secure it in place. In addition to providing structural support, some stents have often been coated with various medications for such purposes as minimizing inflammation and providing treatment. Examples of commonly used coronary stents are described in "Handbook of Coronary Stents", 2nd ed. By Patrick W. Serruys and Michael J. B. Kutryk Eds. (1997, 1998). In addition some stents have been coated with vascular endothelium to lessen clotting and decrease stenosis.

In U.S. Pat. No. 7,044,965 B1, I have disclosed a stent and method of transplanting living cells in a vascular stent.

In U.S. Pat. No. 6,398,804 B1, I disclosed a coronary stent with ports to provide direct blood flow to the myocardium.

In the present invention, I provide a new technology to further the therapeutic effectiveness of both patents.

SUMMARY OF THE INVENTION

Accordingly, it is an object of my invention to facilitate therapeutic cell implantation in animal and human bodies.

Further, it is an object of my invention to enable therapeutic cell implantation at a wide variety of vascular and non-vascular sites within a body with minimal surgery.

Still another object of my invention is to facilitate therapeutic cell engraftment on the surface or the interior of tissues or organs.

Still another object of my invention is to provide a means of transplanting cells producing hormones, useful metabolites, genes, or medications directly to bodily sites where they would be most efficacious.

Still another object of my invention is to effectively supply stem cells or autologous (bone marrow) cells directly to areas of organ injury, to thereby facilitate repair of the injured organ (e.g. heart, liver, pancreas, kidney).

Still another object of my invention is to therapeutically treat abnormal blood vessels, such as aneurysms.

In accordance with my invention I provide a stent for engagement in a bodily structure containing living therapeutic cells. The cells are sealed in a well or wells until the stent is deployed, at which time the seal is broken and the cells are engrafted directly onto and into tissue or organ to be treated. Cells may be nourished from the vascular placement of the stent; cells implanted within the tissue or organ may be nourished by the micro-circulation within the tissue or organ, as well as by the circulation in the case of a vascular stent.

The cells may be isolated cells that have been harvested for this purpose, or they may be part of living tissue. Examples of cells that are appropriate for this purpose are cells that produce useful metabolic products, such as B-glucocerebrosidase for the treatment of Gauchers disease, hormones such as insulin for the treatment of diabetes, mast cells producing heparin, as well as stem cells for the regeneration of cardiac and other organs. Other cellular examples include parathyroid cells, genetically transfected cells, nuclear transferred cells, myocardial cells, liver cells, renal cells, vascular cells, muscle cells, fat cells, bone marrow and hematopoetic cells, progenitor cells, gastrointestinal cells, and smooth muscle cells.

During implantation or insertion into a patient, the cells are retained in the wells by inner and outer membranes. The inner membrane (i.e., the membrane on the inner side of the stent) may be permeable or impermeable; it deforms under pressure applied to it from the inside of the stent to push the cells outwardly of the stent. The outer membrane is of a frangible material, e.g., a thin plastic; it is preferably embedded in a softer perimetral mount (e.g., an O-ring) which retains it in position until the seal is to be broken.

The outer membrane has lines of weakening (e.g., score lines or minute perforations) along which it fractures and opens outwardly when pressure is applied thereto from the interior of the well. The thus-fractured membrane is impaled into the tissue or organ against which it is located, thus facilitating entrance of the cells into the interior of the tissue or organ.

The membrane may be broken by positioning a balloon in the interior of the stent and inflating it opposite the inner membrane. This compresses the inner membrane thereby forcing the cellular contents within the well against the outer membrane and causing it to fracture along the predefined perforations or score lines. The fractured sections hinge or pivot outwardly in the perimetral mount and pierce the tissue or organ so as to deliver the cellular contents to it.

The stent of the present invention provides more flexibility in the selection of implant sites than just a vascular stent. For example, if the object is to engraft cells in the liver, the stent may be implanted in a bile duct, hepatic artery, or portal vein. In the case of the kidney, the stent could be placed in the renal artery or vein or renal pelvis. In other cases, the stent with its charge of therapeutic cells may be implanted at any convenient site in the body for systemic transport of cell products over a broader area; or alternatively, to service a particular organ. Moreover, the stent may be constructed of a biodegradable substance such as catgut or a polymer, so that it disappears, leaving the transplanted cells engrafted on the surface or the interior of the treated tissue or organ.

DETAILED DESCRIPTION OF AN ILLUSTRATIVE EMBODIMENT

Figure 1:
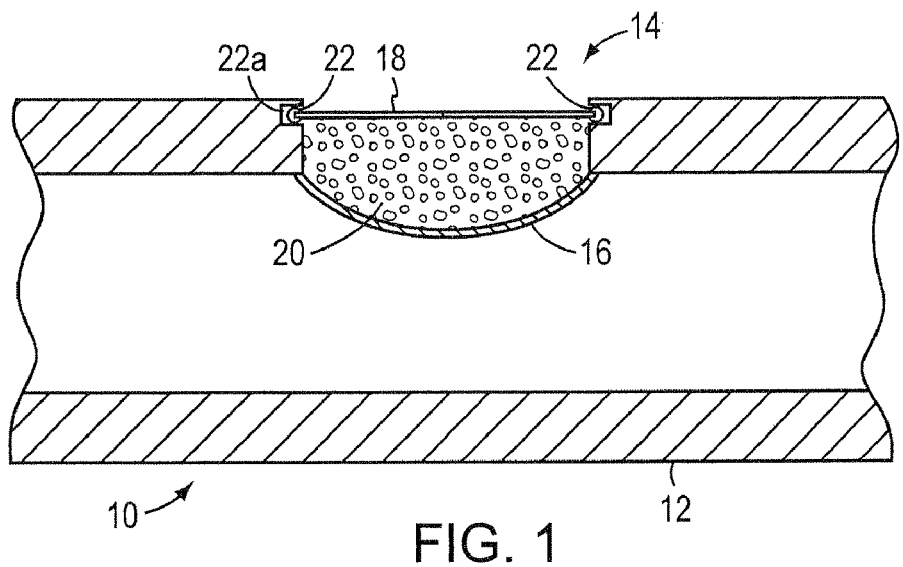
FIG. 1 is a side sectional view of an illustrative embodiment of the present invention showing a stent having an well or chamber in the wall thereof in which cellular material is carried.
Figure 2:
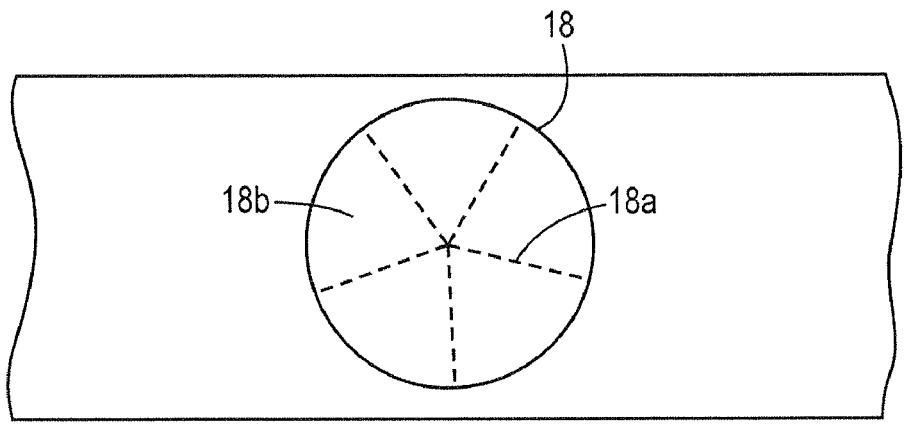
FIG. 2 is a top plan view of the stent of FIG. 1.

In FIG. 1, an illustrative stent 10 in accordance with the present invention has a tubular body 12 having one or more enclosed wells or chambers 14 formed at one or more portions of the tubular wall. The well 14 is formed from an aperture extending through the wall and enclosed by inner and outer membranes 16 and 18, respectively, to form a sealed chamber in cellular material is contained. The inner membrane 16 is in the form of a generally continuous sheet of a pliable plastic of sufficient resilience and strength to deform, but not break, when pressure is applied thereto. It may advantageously take the form of a mesh or microporous membrane in the case of a vascular stent, where the cells will be nourished in part or wholly by the blood flow, or a solid impermeable membrane may be deployed in the case of certain non-vascular stents (e.g. bile ducts or ureter) where the cells are nourished by the microcirculation in the interior of the tissue or organ, and might be harmed by exposure to bile or urine. Alternatively, if a purpose of the cell is to produce bile or urine, a permeable membrane would be used.

The outer membrane 18 is provided in the shape of a thin frangible body, preferably of a thin, hard plastic, and preferably having a plurality of score lines, perforations, or other lines or weakening 18a formed therein. The membrane is preferably embedded in a perimetral mount 22 of a soft, pliable material in the shape of a ring such as an O-ring that is held within a groove 24 in the wall of the stent. The mount retains the outer membrane 18 in position but, when sufficient pressure is applied to the membrane to fracture it into segments, e.g., wedge-shaped segments 18b, the pressure causes the segments to pivot outwardly against and into the tissue or organ that it abuts. These segments have sharp protrusive edges which can penetrate into a body part with which they come into contact, thereby ensuring injection of the cellular material into the body part. The membrane 18 may, but need not be, tapered from its outer edge toward the center thereof.

The stent is used by inserting it into a body part, such as an artery or vein, or by positioning it adjacent an organ, or tissue. The stent is inserted into a patient in the manner of a conventional stent, but may also be implanted in new locations. When positioned at the desired location, a balloon or other force-applying object is inserted into the stent and expanded against the inner membrane 16. This causes the membrane to push outwardly from the center of the stent and thus exerts outward pressure on the outer membrane 18 via the cells 20. At a sufficient pressure, the outer membrane ruptures and releases the cellular contents of the well to the surrounding body tissue, organ or other structure. Because of its frangible nature, the membrane 18 ruptures along the score lines or lines of weakening 18a, thereby forming sharp segments which pierce into the body tissue, organ or other structure against which the membrane is positioned, and ensure discharge of the cellular contents into the interior thereof.

Figure 3:
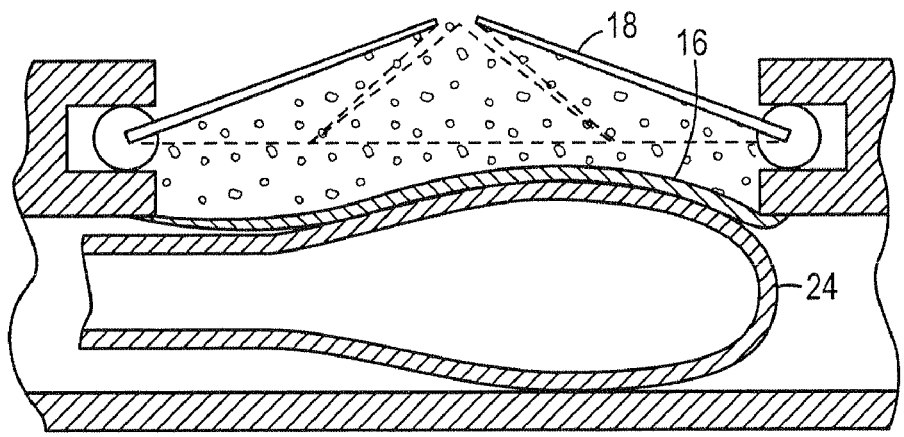
FIG. 3 is a side sectional view of the stent of FIGS. 1 and 2 showing a balloon rupturing the outer membrane.

This is shown in FIG. 3 which is a side sectional view of the stent showing a balloon 24 in inflated condition opposite the well. The pressure of the balloon against the cellular contents has fractured the outer membrane 18 into a number of pie-shaped segments which pivot outwardly in the resilient member 22 and penetrate the tissue or organ.

The cells engraft and generate therapeutic products and engage in exchange of cell and body products either within the treated tissue or organ and/or the blood stream. Nutrients are derived from the treated tissue microincirculation and or the blood stream while metabolic products, hormones, genes, and medication pass directly to the treated tissue or organ or via the microporous membrane into the blood stream. In general, any therapeutic substance that can be manufactured or transported by any cell may be used in the stent of the present invention. In addition, cells from the same patient may be used for auto transplantation, such as parathyroid cells, islet cells and stem cells for example. Cells may be harvested and prepared by growing them in tissue culture, as well as genetically transfected or subjected to nuclear transfer, as well as cells derived from other human or animal sources. Cells from animal sources may have been bred without MHC components, or otherwise modified to prevent rejection. Moreover, any cell susceptible to rejection may be used in this cellular stent in combination with anti-rejection medications.

Cellular tissue may be harvested from an animal source, grown in tissue culture, or assembled by adding the desired cells to adhesion peptides or proteins, such as contained in extra-cellular matrices, as well as collagen, fibronectin, and laminin. Cells may first be embedded in polymeric film or microvelcro, creating hybrid tissue to be deployed by the stent. Adhesives, such as fibronectin may be used to adhere the cells to the stent surface. Also, the stent can advantageously be microfabricated using the techniques of manufacturing surface topographies favorable to cell adhesion creating pillars, and holes, micro-grooves, cavities, bumps, microvelcro, and immunocontact printing of self-attachment. Laser writing may be used for cell placement. Protein patterning and surface modification with polymers may be used.

The stent of the present invention provides wide latitude in the placement within a body and enables the engraftment of therapeutic cells on the surface or interior of various tissues and organs producing a unique scaffold for cellular transplantation.

It will be understood that various changes can be made in the specific embodiment described and shown herein without departing from either the spirit or scope of the invention with the invention being defined specifically in the claims.

What is claimed is:

1. A stent for implantation in an animal or human body, said stent having an outer face for lodging against the surface of a tissue or organ and an inner face, said stent comprising:
   (a) one or more wells adapted for carrying living therapeutic cells, said wells extending through the outer face of said stent to said inner face;
   (b) a first frangible; tissue-or-organ-penetrable membrane comprising a rigid frangible material at the outer face of each well for confining cells therein, said membrane embedded in a pliable perimetral mount and having lines of weakening therein, said membrane formed to fracture along said lines of weakening under sufficient pressure into sharp segments that pivot outwardly from the well and pierce the surface of the tissue or organ in order to deposit cells into its interior; and
   (c) a second membrane at said inner face of each well, said membrane being either permeable for vascular applications or impermeable for non-vascular applications.

2. A stent according to claim 1 wherein the second membrane is porous to permit products produced by said cells to enter the blood stream, urinary tract, or bile duct.

3. A stent according to claim 1 wherein the second membrane is non-porous.

4. A stent according to claim 1 wherein said cells produce products comprising one or more of a hormone, a metabolic substance, a medication, and a gene.

5. A stent according to claim 1 wherein the second membrane comprises a mesh of sufficient porosity to admit cell nutrients into the well.

6. A stent according to claim 1 wherein the second membrane is microporous.

7. A stent according to claim 1 wherein said cells are disposed in a strip of cellular tissue harvested from an animal surface or human.

8. A stent according to claim 1 wherein said cells are disposed in polymeric films.

9. A stent according to claim 1 in which said second membrane is permeable so that nutrients from blood in a blood vessel can pass through said membrane and sustain the cells after transplantation.

10. A stent according to claim 1 wherein said second membrane is impermeable so that the cells are sustained after transplantation by nutrients from blood in the micro-circulation of the treated tissue or organ.

11. A stent according to claim 1 wherein said cells comprise one or more types of cells selected from the group consisting of endocrine cells, islet cells, mast cells, stem cells, parathyroid cells, genetically transfected cells, nuclear transferred cells, myocardial cells, liver cells, renal cells, vascular cells, muscle cells, fat cells, bone marrow and hematopoietic cells, progenitor cells, gastrointestinal cells, and smooth muscle cells.

12. A method for providing living therapeutic cells in an animal or human body comprising:
   (a) implanting in said body a stent carrying a charge of living therapeutic cells in one or more wells therein, said wells extending from an outer face of said stent to an inner face thereof;
   (b) retaining said cells with a frangible first membrane at the outer face of each well for confining cells therein, said membrane comprising a rigid frangible material embedded in a pliable perimetral mount and having lines of weakening therein, said membrane formed to fracture along said lines of weakening under sufficient pressure into sharp segments that pivot outwardly from the well and pierce the surface of the tissue or organ in order to deposit cells into its interior;
   (c) providing a second membrane at said inner face of each well, said membrane being either permeable for vascular applications or impermeable for non-vascular applications.

13. The method of claim 12 further comprising delivering products produced by said cells to said body through said second membrane, including urine and bile, as well as by the blood stream.

14. The method of claim 12 further comprising, selecting therapeutic cells wherein said cells produce one or more products selected from the group consisting of a hormone, a metabolic substance, a medication, and a gene.

15. The method of claim 12 further comprising a charge of living therapeutic cells.

16. The method of claim 15 in which said charge of living therapeutic cells includes strips of cellular tissue harvested from an animal or human source.

17. The method of claim 15 in which said charge of living therapeutic cells includes strips of cellular tissue or cells grown in tissue culture.

18. The method of claim 12 in which said charge of living therapeutic cells includes cells disposed on polymeric films.

19. The method of claim 12 wherein said nutrients are from blood in said blood vessel and said nutrients sustain said cells after implementation.

20. The method of claim 12 wherein said nutrients are from blood in the micro-circulation of the treated tissue or organ.

21. The method of claim 12 in which part or all of the stent is biodegradable.

* * * * *